US008440390B2

(12) United States Patent
Brockbank (10) Patent No.: US 8,440,390 B2
(45) Date of Patent: May 14, 2013

(54) METHOD FOR ICE-FREE CRYOPRESERVATION OF TISSUE

(75) Inventor: Kelvin G. M. Brockbank, North Charleston, SC (US)

(73) Assignees: Lifeline Scientific, Inc., Itasca, IL (US); Cell & Tissue Systems, Inc., North Charleston, SC (US)

( * ) Notice: Subject to any disclaimer, the term of this patent is extended or adjusted under 35 U.S.C. 154(b) by 440 days.

(21) Appl. No.: 12/710,957

(22) Filed: Feb. 23, 2010

(65) Prior Publication Data

US 2010/0216110 A1    Aug. 26, 2010

Related U.S. Application Data

(60) Provisional application No. 61/154,495, filed on Feb. 23, 2009.

(51) Int. Cl.
*A01N 1/00* (2006.01)
(52) U.S. Cl.
USPC .......................................................... 435/1.1
(58) Field of Classification Search .................. None
See application file for complete search history.

(56) References Cited

U.S. PATENT DOCUMENTS

| | | | |
|---|---|---|---|
| 4,494,385 A | 1/1985 | Kuraoka et al. |
| 4,559,298 A | 12/1985 | Fahy |
| 5,122,110 A | 6/1992 | McNally et al. |
| 5,145,769 A | 9/1992 | McNally et al. |
| 5,149,621 A | 9/1992 | McNally et al. |
| 5,158,867 A | 10/1992 | McNally et al. |
| 5,217,860 A | 6/1993 | Fahy et al. |
| 5,242,792 A | 9/1993 | Rudolph et al. |
| 5,472,876 A | 12/1995 | Fahy |
| 5,518,878 A | 5/1996 | Wilkins et al. |
| 5,629,145 A | 5/1997 | Meryman |
| 5,648,206 A | 7/1997 | Goodrich et al. |
| 5,723,282 A | 3/1998 | Fahy et al. |
| 5,821,045 A | 10/1998 | Fahy et al. |
| 5,827,741 A | 10/1998 | Beattie et al. |
| 5,856,081 A | 1/1999 | Fahy |
| 5,873,254 A | 2/1999 | Arav |
| 5,955,448 A | 9/1999 | Colaco et al. |
| 5,962,214 A | 10/1999 | Fahy et al. |
| 6,127,177 A | 10/2000 | Toner et al. |
| 6,187,529 B1 | 2/2001 | Fahy et al. |
| 6,194,137 B1 | 2/2001 | Khirabadi et al. |
| 6,274,303 B1 | 8/2001 | Wowk et al. |
| 6,395,467 B1 | 5/2002 | Fahy et al. |
| 6,740,484 B1 | 5/2004 | Khirabadi et al. |
| 6,770,478 B2 | 8/2004 | Crowe et al. |
| 2005/0100876 A1 | 5/2005 | Khirabadi et al. |
| 2005/0277107 A1 | 12/2005 | Toner et al. |

FOREIGN PATENT DOCUMENTS

| | | |
|---|---|---|
| EP | 1 471 140 A1 | 10/2004 |
| WO | WO 96/05727 | 2/1996 |
| WO | WO 00/60935 | 10/2000 |
| WO | WO 01/78504 | 10/2001 |
| WO | WO 02/32225 A2 | 4/2002 |
| WO | WO 2005/027633 A2 | 3/2005 |

OTHER PUBLICATIONS

Brockbank et al., "Quantitative second harmonic generation imaging of carilage damage", Cell Tissue Banking 9: 299-307 (2008).*
Brockbank et al., "57. Comparison of heart valve cyropreservation and storage methods," Cryobiology, Nov. 22, 2007, pp. 342-343, vol. 55, No. 3, Academic Press Inc, US.
Oct. 11, 2011 International Preliminary Report on Patentability issued in PCT/US2010/025086.
Oct. 7, 2011 Written Opinion issued in PCT/US2010/025086.
Oct. 7, 2011 International Search Report issued in PCT/US2010/025086.
Schenke-Layland et al., "Optimized Preservation of Extracellular Matrix in Cardiac Tissues: Implications for Long-Term Graft Durability," The Annals of Thoracic Surgery, Apr. 24, 2007, pp. 1641-1650, vol. 83, No. 5, Elsevier Inc.
Schenke-Layland et al., "Impact of Cryopreservation on Extracellular Matrix Structures of Heart Valve Leaflets," The Annals of Thoracic Surgery, Mar. 1, 2006, pp. 918-926, vol. 81, No, 3, Elsevier Inc.
Xu H et al., "An experimental research on cryopreserving rabbit trachea by vitrification," Cryobiology, Apr. 1, 2009, pp. 225-231, vol. 58, No. 2, Academic Press Inc.
Kuleshova et al., "Vitrification as a prospect for cryopreservation of tissue-engineered constructs," Biomaterials, Jan. 14, 2007, pp. 1585-1596, vol. 28, No. 9, Elsevier Science Publishers.
Song et al., "Vitreous Cryopreservation Maintains the Function of Vascular Grafts," *Nature Biotechnology*, vol. 18, pp. 296-299, Mar. 2000.

(Continued)

Primary Examiner — Sandra Saucier
(74) Attorney, Agent, or Firm — Oliff & Berridge, PLC (57) ABSTRACT

Method for preserving tissue including immersing the tissue in a solution having a cryoprotectant concentration of at least 75% by weight, a cooling step where the tissue is cooled to a temperature between the glass transition temperature of the solution having a cryoprotectant concentration of at least 75% by weight and −20° C., a storage step where the tissue is stored at a temperature between the glass transition temperature of the solution and −20° C., a rewarming step, where the tissue is warmed, and a washing step.

26 Claims, 3 Drawing Sheets
(2 of 3 Drawing Sheet(s) Filed in Color)

OTHER PUBLICATIONS

Polce et al., "Revival of Spermatozoa after Vitrification and Dehydration at Low Temperatures," *Nature*, vol. 164, p. 666, Oct. 1949.

Lovelock et al., "Prevention of Freezing Damage to Living Cells by Dimethyl Sulphoxide," *Nature*, vol. 183, pp. 1394-1395, May 1959.

Brockbank et al., "Synergistic Interaction of Low-Molecular-Weight Polyvinylpyrrolidones with Dimethylsulfoxide During Cell Cryopreservation," *Transplantation Proceedings*, vol. 25, No. 6, pp. 3189-3191, Dec. 1993.

Crowe et al., "The Role of Vitrification in Anhydrobiosis," *Annu. Rev. Physiol.*, vol. 60, pp. 73-103, 1998.

Potts, "Desiccation Tolerance of Prokaryotes," *Microbiological Reviews*, vol. 58, No. 4, pp. 755-805, Dec. 1994.

Crowe et al., "Interactions of Sugars with Membranes," *Biochimica et Biophysica Acta*, vol. 947, pp. 367-384, 1988.

Crowe et al., "Anhydrobiosis," *Annu. Rev. Physiol.*, vol. 54, pp. 579-599, 1992.

Womersley et al., "Inhibition of Dehydration-Induced Fusion between Liposomal Membranes by Cartohydrates as Measured by Fluorescence Energy Transfer," *Cryobiology*, vol. 23, pp. 245-255, 1986.

De Castro et al., "Anhydrobiotic Engineering," *Nature Biotechnology*, vol. 18, p0. 473, May 2000.

Eroglu et al., "Intracellular Trehalose Improves the Survival of Cryopreserved Mammalian Cells," *Nature Biotechnology*, vol. 18, pp. 163-167, Feb. 2000.

Beattie et al., "Trehalose: A Cryoprotectant That Enhances Recovery and Preserves Function of Human Pancreatic Islets after Long-Term Storage", *Diabetes*, vol. 46, pp. 519-523, Mar. 1997.

Acker et al., "Tissue Engineering," *Science & Medicine*, pp. 126-127, May/Jun. 2000.

Guo et al., "Trehalose Expression Confers Desiccation Tolerance on Human Cells," *Nature Biotechnology*, vol. 18, pp. 168-170, Feb. 2000.

Gilles et al., "Effect of Compensatory Organic Osmolytes on Resistance to Freeze-Drying of L929 Cells and of their Isolated Chromatin," Comparative Biochemistry and Physiology Part A 122: 145-155 (1999).

Scannell et al., "The Regulation of Carbohydrate Metabolism in Animal Cells: Growth on Starch and Maltose," Biochemical Society Transactions 8 (5) : 633-4 (1980).

Kim et al., "Cryopreservation of Taxus Chinensis Suspension Cell Cultures," CryoLetters 22: 43-50 (2001).

Burger et al. "Transport of Some Mono- and Di-Saccharides Into Yeast Cells," Biochemical Journal 71: 235-42 (1959).

D.E. Pegg et al., "Fractures in Cryopreserved Elastic Arteries," Abstract Only, Database Accession No. PREV199799558143, Cryobiology, vol. 34, No. 2, pp. 183-192, 1997.

Armitage, "Survival of Corneal Endothelium following Exposure to a Vitrification Solution," Cryobiology, vol. 26, 1989, pp. 318-327.

Bourne et al., "Human Corneal Studies with a Vitrification Solution Containing Dimethyl Sulfoxide, Formamide, and 1,2-Propanediol," Cryobiology, vol. 31, No. 6, 1994, pp. 522-530.

Dent et al., "Cryopreservation of Vein Grafts," Surgical Forum, vol. 25, pp. 241-243, 1974.

Brockbank et al., "Cryopreserved Vein Transplantation," Journal of Cardiac Surgery, vol. 7, No. 2, pp. 170-176, 1992.

Müller-Schweinitzer, "Cryopreservation: a useful technique for storing tissues for pharmacological investigations," Trends in Pharmacological Sciences; vol. 9, No. 6, pp. 221-223; Jun. 1988.

Weber et al., "Viable Vein Graft Preservation," Journal of Surgical Research 18, pp. 247-255, 1975.

Bishop et al., "A morphological assessment of vein allografts preserved in glycerol and used for arterial replacement," Journal of Cardiovascular Surgery 28, pp. 491-497, 1987.

Barner et al., "Fresh and Frozen Homologous Venous Grafts for Arterial Repair," Angiology 17, pp. 389-401, 1966.

Sitzmann et al., "Dimethylsulfoxide-treated, cryopreserved venous allografts in the arterial and venous systems," Surgery, vol. 95, No. 2, pp. 154-159, 1984.

Song et al., "Cryopreservation of the Common Carotid Artery of the Rabbit: Optimization of Dimethyl Sulfoxide Concentration and Cooling Rate," Cryobiology 32, pp. 405-421, 1995.

Wusteman et al., "The Effect of Cooling Rate and Temperature on the Toxicity of Ethylene Glycol in the Rabbit Internal Carotid Artery," Cryobiology 33, pp. 423-429, 1996.

Narayanan et al., "Successful Cryopreservation of Microvenous Allografts," Journal of Investigative Surgery, vol. 5, pp. 155-160, 1992.

Ku et al., "Human Coronary Vascular Smooth Muscle and Endothelium-Dependent Responses after Storage at −75° C," Cryobiology 29, pp. 199-209, 1992.

Müller-Schweinitzer et al., "Sucrose promotes the functional activity of blood vessels after cryopreservation in DMSO-containing fetal calf serum," Naunyn-Schmiedeberg's Archives of Pharmacology, pp. 1-4, 1992.

Mëller-Schweinitzer et al., "Functional recovery of human mesenteric and coronary arteries after cryopreservation at −196° C in a serum-free medium," Journal of Vascular Surgery, vol. 25, No. 4, pp. 743-749, 1997.

Fahy et al., G. M., "Vitrification as an Approach to Cryopreservation," Cryobiology 21, pp. 407-426, 1984.

Chen et al., X. H., "Vitrification of Multicomponent Solutions by Cooling to Cryogenic Temperatures," Cryogenics vol. 30 Sept. Supplement, pp. 541-545, 1990.

Fahy et al., G. M., "Some Emerging Principles Underlying the Physical Properties, Biological Actions, and Utility of Vitrification Solutions," Cryobiology 24, pp. 196-213, 1987.

Ren et al., H. S., "The Crystallization Kinetics and the Critical Cooling Rates for Vitrification of Cryoprotective Solutions," Cryogenics 1990, vol. 30, September Supplement, pp. 536-540.

Guttman et al., Frank M., "Variation of Cooling Rate and Concentration of Dimethyl Sulfoxide on Rabbit Kidney Function," Cryobiology, 23, pp. 495-499, 1986.

Jacobsen et al., I.A., "Effect of Cooling and Warming Rate on Glycerolized Rabbit Kidneys," Cryobiology 19:668, 1982.

* cited by examiner

METHOD FOR ICE-FREE CRYOPRESERVATION OF TISSUE

CROSS-REFERENCE TO RELATED APPLICATION

This nonprovisional application claims the benefit of U.S. Provisional Application No. 61/154,495 filed Feb. 23, 2009. The disclosure of the prior application is hereby incorporated by reference in its entirety.

TECHNICAL FIELD

The invention relates to a method for preserving tissues. More specifically, the invention relates to a method for preserving tissue matrices by employing high concentrations of cryoprotective chemicals. The invention is applicable to applications of intact extracellular tissue matrices that do not require living or viable cells.

BACKGROUND

Low temperature preservation of biological tissues such as organs, i.e., cryopreservation, has been the subject of much research effort. Cryopreservation may be approached by freezing or by vitrification. If the tissue is frozen, ice crystals may form within the tissue that may mechanically disrupt its structure and thus damage its ability to function correctly when it is transplanted into a recipient. Organized tissues are particularly susceptible to mechanical damage from ice crystals formed during freezing.

Cryopreserved human and animal tissues are used in a variety of medical applications. In particular, transplantation of cryopreserved heart valves (allografts) represents a well-established valve replacement option. See O'Brien, M. F., Harrocks, S., Stafford, E. G. et al., J Heart Valve Dis 10:334-344 (2001).

However, application of this treatment concept is limited by degeneration and long-term failure, and complicated due to expensive preservation, storage and shipping infrastructures. See Mayer, J. E. Jr., Sem Thorac Cardiovasc Surg 7:130-132 (1995).

Even when all cryopreservation variables are controlled, there is a limit, which is largely a function of tissue volume and geometry (including any associated fluids and packaging), beyond which traditional cryopreservation methods do not consistently work. For example, in cryopreserved allograft heart valves, the leaflet fibroblasts survive well (70-90%), but neither the endothelial cells nor the smooth muscle cells of the aortic tissue associated with the valve survive. The problems include ice formation either within the cells, the extracellular matrix, the capsule, or, as in the case of heart valve endothelium, compression in the lumen of the associated artery.

Transplantation of allograft heart valves was first clinically introduced in 1962. See Ross, D., Lancet 12:487 (1962). Allograft heart valves have been shown to demonstrate exceptionally good initial hemodynamic characteristics, hardly any thromboembolic events without anticoagulation and better resistance to endocarditis compared to bioprosthetic or mechanical valve substitutes. See O'Brien, M., Stafford, E., Gardner, M., Pohlner, P., McGiffin, D., J Thorac Cardiovasc Surg 94:812-23 (1987); see also Tuna, I. C., Orszulak, T A, Schaff, R V., Danielson, G. K., Ann Thorac Surg 49:619-24 (1990).

Initially, the valves were collected and immediately transplanted as so-called homovitals. See Gonzalez-Lavin, L., McGrath, L. B., Amini, S., Graf, D., J Card Surg 3:309-12 (1988). Due to logistic issues, grafts were subsequently stored at 4° C. in tissue culture medium with antibiotics for up to 6 weeks prior to implantation. See Jonas, R. A., Ziemer, G., Britton, L., Armiger, L. C., J Thorac Cardiovasc Surg 96:746-55 (1988).

Eventually, in order to enable long-term storage and improve safety by means of microbiology and virology, cryopreservation with controlled rate freezing and storage in vapor phase nitrogen was introduced. See Watts, L. K., Duffy, P., Field, R. B., Stafford, E. G., O'Brien, M. F., Ann Thorac Surg, 21:230-6 (1976). For the last 20 years frozen cryopreservation (FC) has been the worldwide choice for preservation of human heart valves. See Standards for Tissue Banking, 11th Edition, American Association of Tissue Banks, 2006.

The FC methods employed a strategy where ice formation was encouraged because ice formation is a critical part of the freezing process. See Schenke-Layland, K., Madershahian, N., Riemann, I. et al., Ann Thorac Surg 81:918-26 (2006). Long-term function of cryopreserved heart valves (allografts) is limited by immune responses, inflammation, subsequent structural deterioration and an expensive infrastructure. See Mitchell, R. N., Jonas, R. A., Schoen, F. J., J Thorac Cardiovasc Surg 115:118-27 (1998); see also; Mayer, J. E. Jr., Sem Thorac Cardiovasc Surg 7:130-132 (1995)

The durability of contemporary cryopreserved allograft valves varies from 50% to 90% at 10 to 15 years. See O'Brien, M. F., Harrocks, S., Stafford, E. G. et al., J Heart Valve Dis 10:334-344 (2001). In particular, in pediatric patients allograft function is limited by earlier and faster structural deterioration necessitating more frequent re-intervention procedures. Bonhoeffer, P., Boudjemline, Y., Saliba, Z. et al., Lancet 356:1403-5 (2000); see also Joudinaud, T. M. et al., Eur J Cardiothorac Surg 33:989-94 (2008). A variety of mechanisms for this increased structural deterioration have been proposed including T-cell mediated inflammation. See Legare J F, Lee T D, Creaser K, Ross D B, Ann Thorac Surg. 70:1238-45 (2000).

Another potential mechanism is the freezing and storage process itself. Although it has been previously shown that FC accelerates degeneration in a syngeneic rodent model, the direct impact of ice formation on elastic and collagenous fiber containing tissues could not be displayed conclusively using conventional visualization methods. 14. Legare, J. F., Lee, D. G., Ross, D. B., Circulation 102: III75-78 (2000). The development and application of multiphoton-induced autofluorescence and SHG imaging has allowed visualization of ECM alterations with submicron resolution. See Schenke-Layland, K., et al., Ann Thorac Surg 81:918-26 (2006); see also Schenke-Layland, K. et al., Ann Thorac Surg 83:1641-50 (2007)

Studies utilizing multiphoton imaging (MI) methodologies have demonstrated that conventional FC by controlled freezing is accompanied by serious alterations of extracellular matrix (ECM) structures. See Schenke-Layland, K., Madershahian, N., Riemann, I. et al., Ann Thorac Surg 81:918-26 (2006).

Vitreous cryopreservation (VC) has been identified as an alternative preservation approach that avoids ice formation and preserves ECM in vitro. See Song, Y. C., Khirabadi B. S., Lightfoot, F. G., Brockbank, K. G. M., Taylor, M. J., Nature Biotech 18: 296-299 (2000); see also Schenke-Layland, K., Xie, J., Hagvall, S. H. et al., Ann Thorac Surg 83:1641-50 (2007).

Vitrification means solidification, as in a glass, without ice crystal formation. Principles of vitrification are well known.

Generally, the lowest temperature a solution can possibly supercool to without freezing is the homogeneous nucleation temperature $T_h$, at which temperature ice crystals nucleate and grow, and a crystalline solid is formed from the solution. Vitrification solutions have a glass transition temperature $T_g$, at which temperature the solute vitrifies, or becomes a non-crystalline solid. Owing to the kinetics of nucleation and crystal growth, it is effectively impossible for water molecules to align for crystal formation at temperatures much below $T_g$. In addition, on cooling most dilute aqueous solutions to their glass transition temperature, $T_h$ is encountered before $T_g$, and ice nucleation occurs, which makes it impossible to vitrify the solution. In order to make such solutions useful in the preservation of biological materials by vitrification, it is therefore necessary to change the properties of the solution so that vitrification occurs instead of ice crystal nucleation and growth.

While it is generally known that high hydrostatic pressures raise $T_g$ and lower $T_h$, vitrification of most dilute solutions by the application of pressure is often impossible or impractical. In particular, for many solutions vitrifiable by the application of pressure, the required pressures cause unacceptably severe injury to unprotected biomaterials during vitrification thereof. While it is also known that many solutes, such as commonly employed cryoprotectants like DMSO, raise $T_g$ and lower $T_h$, solution concentrations of DMSO or similar solutes high enough to permit vitrification typically approach the eutectic concentration and are generally toxic to biological materials.

SUMMARY OF THE INVENTION

Embodiments include a method for preserving a tissue, comprising immersing the tissue in a solution having a cryoprotectant concentration of at least 75% by weight, and cooling the tissue in the solution having said cryoprotectant concentration of at least 75% by weight to a temperature between about −20° C. and the glass transition temperature of the solution having said cryoprotectant concentration of at least 75% by weight.

Embodiments include a method for preserving a tissue, comprising immersing the tissue in a series of solutions having increasing concentrations of cryoprotectant to achieve immersion in a final solution with a cryoprotectant concentration of at least 75% by weight, and cooling the tissue in the solution having said cryoprotectant concentration of at least 75% by weight to a temperature between about −20° C. and the glass transition temperature of the solution having said cryoprotectant concentration of at least 75% by weight.

The present disclosure addresses these needs by providing an ice-free cryopreservation method to preserve extracellular matrix integrity, diminish immune response and improve long-term function of mammalian tissue, such as allograft heart valves, for implantation.

BRIEF DESCRIPTION OF THE DRAWINGS

This patent application contains at least one drawing executed in color.

FIG. 1A shows frozen cryopreserved (FC) heart valve with thickening of the leaflets (arrows). FIG. 1B shows ice-free cryopreserved (IFC) heart valve with normal appearance of the leaflets.

DETAILED DESCRIPTION OF EMBODIMENTS

An ice-free cryopreservation (IFC) method for preserving tissues, such as intact extracellular tissue matrices that do not require living or viable cells, may comprise: immersing the tissue in a solution having a cryoprotectant concentration of at least 75% by weight or immersing the tissue in a series of solutions with the final solution having a cryoprotectant concentration of at least 75% by weight; and single, gradient, or stepwise cooling step, wherein the tissue is cooled to a temperature between the glass transition temperature of the first solution and −20° C.; a storage step, wherein the tissue is stored at temperature between the glass transition temperature of the cryoprotectant solution and −20° C.; an optional rewarming step, wherein the tissue is warmed in a single, gradient, or stepwise rewarming step; and an immersion or washing step occurring during or after the rewarming step, where the cryoprotectant is washed out of the tissue in a single, gradient or multiple steps.

"Tissue" is used herein to refer to any natural or engineered biological extracellular tissue matrices that do not require living, viable cells, including extracellular tissue matrices of vascularized tissues and avascular tissues, including vascular tissue, such as blood vessels, musculoskeletal tissue, such as cartilage, menisci, muscles, ligaments and tendons, skin, cardiovascular tissue, such as heart valves and myocardium, periodontal tissue, peripheral nerves, gastro-intestinal tract tissues, ureter and urethra. "Blood vessel" is used herein to refer to any biological tube conveying blood. Thus, the phrase refers inter alia to an artery, capillary, vein, sinus or engineered construct.

As used herein, the term "transplantation" refers to any type of transplantation or implantation whether or not autologous, homologous or heterologous, and whether or not it is performed directly or subsequent to further processing of the tissue.

As used herein, the term "vitrification" refers to solidification without ice crystal formation. As used herein, a tissue is vitrified when it reaches the glass transition temperature (Tg). The process of vitrification involves a marked increase in viscosity of the cryoprotectant solution as the temperature is lowered such that ice nucleation and growth are inhibited. In practice, vitrification or vitreous cryopreservation may be achieved even in the presence of a small, or restricted amount of ice, which is less than an amount that causes injury to the tissue.

As used herein, the "glass transition temperature" refers to the glass transition temperature of a solution or formulation under the conditions at which the process is being conducted. In general, the process of the present invention is conducted at physiological pressures. However, higher pressures can be used as long as the tissue is not significantly damaged thereby.

As used herein, "physiological pressures" refer to pressures that tissues undergo during normal function. The term "physiological pressures" thus includes normal atmospheric conditions, as well as the higher pressures that various tissues, such as vascularized tissues, undergo under diastolic and systolic conditions.

As used herein, the term "perfusion" means the flowing of a fluid through the tissue. Techniques for perfusing organs and tissues are discussed in, for example, U.S. Pat. No. 5,723,282 to Fahy et al., which is incorporated herein in its entirety.

As used herein, the term "cryoprotectant" means a chemical that minimizes ice crystal formation in a tissue when the tissue is cooled to subzero temperatures and results in substantially no damage to the tissue after warming, in comparison to the effect of cooling without cryoprotectant.

As used herein, the term "substantially cryoprotectant-free tissue" refers to a tissue having substantially no cryoprotectant therein, such as a tissue containing less than 2% by weight cryoprotectant, or a tissue having less than 1% by weight cryoprotectant, or a tissue having less than 0.1% by weight cryoprotectant. As used herein, the term "cryoprotectant-free tissue" refers to a tissue having no cryoprotectant therein.

As used herein, the term "substantially cryoprotectant-five solution" refers to a solution having substantially no cryoprotectant therein, such as a solution containing less than 1% cryoprotectant by weight, or a solution having less than 0.5% cryoprotectant by weight, or a solution having less than 0.1% cryoprotectant by weight. As used herein, the term "cryoprotectant-free solution" refers to a solution having no cryoprotectant therein.

As used herein, "approximate osmotic equilibration" means that there is no more than a 10% difference between the intracellular and extracellular solute concentrations, such as no more than a 5% difference between the intracellular and extracellular solute concentrations. A difference of no more than 10% means, for example, that if the extracellular concentration is 4M, the intracellular solute concentration is between 3.6 and 4.4M.

Vitrification may be achieved using a variety of cryoprotectant mixtures and cooling/warming conditions. The key variables should be optimized for each particular extracellular tissue matrix type and sample size. The choice of cryoprotectant mixtures and the equilibration steps necessary for cryoprotectant addition and removal without undue osmotic shock should be optimized based upon measured kinetics of cryoprotectant permeation in tissue samples. Cryosubstitution can also be employed to verify that ice-free preservation has been achieved for a given protocol.

Embodiments may comprises a single or a stepwise cooling process, such as, when the tissue is cooled (at a constant rate) in a first solution containing cryoprotectant at temperature between the glass transition temperature of the first solution and −20° C.; and a storage step, wherein the tissue is stored at temperature between the glass transition temperature of the first solution and −20° C.

The single cooling step may also be performed in a single step of decreasing the temperature of the tissue where the rate of cooling stays constant, or changes by either increasing or decreasing. Alternatively, the tissue may be cooled in a stepwise cooling process in which the temperature of the tissue is decreased to a first temperature in a first solution containing cryoprotectant at a first temperature between the glass transition temperature of the first solution and −20° C., then is further decreased to a second temperature in a second solution containing cryoprotectant at temperature between the glass transition temperature of the first solution and −20° C., and this process may be repeated with a third, forth, fifth, sixth, seventh, etc., solution until the desired temperature is achieved.

In embodiments, the glass transition temperature of the first solution (cryoprotectant solution formulation) is in the range from about −100° C. to about −140° C., such as about −110° C. to about −130° C., or −115° C. to about −130° C., for example about −124° C. In embodiments, the tissue may be cooled and subsequently stored at temperatures between the glass transition temperature and about −20° C., such as about −120° C. to about −20° C., such as between about −110° C. to about −30° C., or between about −90° C. and about −60° C.

During the cooling step and the storage step, it is important to prevent tissue-glass cracking and ice forming. In contrast to other cryopreservation methods, a method for preserving a tissue, such as mammalian tissue, is focused on matrix preservation alone, and the method need not be specifically designed to preserve cells in a viable state.

"Mammalian" is used herein to refer to include any mammal, such as a human.

In embodiments, a single cooling step; a stepwise cooling process at either regular, increasing, or decreasing intervals; or a gradient cooling step in which the rate of cooling is increased or decreased during the cooling process, may be used to cool the tissue to a temperature in the range of about −60° C. to about −100° C., such as −70° C. to about −90° C., for example about −80° C.

By employing a high concentration cryopreservation solution formulation, cooling and storage at a temperature between the glass transition temperature of the cryoprotectant formulation and about −20° C. may be attained without tissue-glass cracking and icing. In embodiments, the first solution contains about 75 wt % or more of cryoprotectant, such as about 80% to about 99% cryoprotectant, or about 83% to about 95% cryoprotectant.

After being immersed in a cryoprotectant-free solution, the tissue may be immersed in a solution containing cryoprotectant with or without perfusion. The final cryoprotectant concentration may be reached in a stepwise cooling process in which the tissue may be immersed in a first solution containing a first cryoprotectant concentration, then the tissue may be immersed in a second solution containing a second cryoprotectant concentration (which is higher than the first cryoprotectant concentration), and this process may be repeated with a third, forth, fifth, sixth, seventh, etc., solution until the desired concentration is achieved. The cryoprotectant solution may contain any combination of cryoprotectants. Cryoprotectants include, for example dimethyl sulfoxide, 1,2-propanediol, ethylene glycol, n-dimethyl formamide and 1,3-propanediol in addition to those listed below in Table 1.

TABLE 1

Acetamide
Agarose
Alginate
Alanine
Albumin
Ammonium acetate
Butanediol
Chondroitin sulfate
Chloroform
Choline
Cyclohexanediols
Dextrans
Diethylene glycol
Dimethyl acetamide
Dimethyl formamide TABLE 1-continued Dimethyl sulfoxide
Erythritol
Ethanol
Ethylene glycol
Ethylene glycol monomethyl ether
Formamide
Glucose
Glycerol
Glycerophosphate
Glyceryl monoacetate
Glycine
Hydroxyethyl starch
Inositol
Lactose
Magnesium chloride
Magnesium sulfate
Maltose
Mannitol
Mannose
Methanol
Methoxy propanediol
Methyl acetamide
Methyl formamide
Methyl ureas
Methyl glucose
Methyl glycerol
Phenol
Pluronic polyols
Polyethylene glycol
Polyvinylpyrrolidone
Proline
Propylene glycol
Propanediol
Pyridine N-oxide
Ribose
Serine
Sodium bromide
Sodium chloride
Sodium iodide
Sodium nitrate
Sodium nitrite
Sodium sulfate
Sorbitol
Sucrose
Trehalose
Triethylene glycol
Trimethylamine acetate
Urea
Valine
Xylose Impermeable cryoprotectant agents such as polyvinylpyrrolidone or hydroxyethyl starch may be more effective at protecting biological systems cooled at rapid rates. Such agents are often large macromolecules, which affect the properties of the solution to a greater extent than would be expected from their osmotic pressure. Some of these non-permeating cryoprotectant agents have direct protective effects on the cell membrane. However, the primary mechanism of action appears to be the induction of extracellular glass formation. When such cryoprotectants are used in extremely high concentrations, ice formation may be eliminated entirely during cooling to and warming from cryogenic temperatures. Impermeable chemicals with demonstrated cryoprotective activity include agarose, dextrans, glucose, hydroxyethylstarch, inositol, lactose, methyl glucose, polyvinylpyrrolidone, sorbitol, sucrose and urea.

In embodiments, the cryoprotectant solution contains dimethyl sulfoxide, formamide, and 1,2-propanediol in a vehicle solution, such as Euro-Collins solution. Such a solution may contain about 75% to about 99% w/v cryoprotectant. The amount of dimethyl sulfoxide may be varied from 20 to 50% w/v. Similarly, the amount of 1,2-propanediol and formamide may each be varied from about 10 to 40% w/v. However, the total amount of cryoprotectant in the full strength solution (or final solution in which the tissue is stored) should be about 75 wt % or more of cryoprotectant, such as about 80% to about 99% cryoprotectant, or about 83% to about 95% cryoprotectant. The molarity of cryoprotectant in a 75 wt % or more of cryoprotectant solution (i.e., the final solution in which the tissue is stored) will depend on the molecular weight of the cryoprotectant. Generally, the molarity of the cryoprotectant solution should be greater than about 6M (6 moles of cryoprotectant per liter of solution) for larger molecular weight cryoprotectants and higher for lower molecular weight cryoprotectants, such as, for example, a concentration of cryoprotectant from about 8M to about 25M, or a concentration of cryoprotectant from about 10M to about 20M, or a concentration of cryoprotectant from about 12M to about 16M.

The cryoprotectant solution may also be modified with conventional cryoprotectants and/or natural or synthetic ice-blocking molecules, for example, acetamide, agarose, alginate, alanine, albumin, ammonium acetate, anti-freeze proteins, butanediol, chondroitin sulfate, chloroform, choline, cyclohexanediols, cyclohexanediones, cyclohexanetriols, dextrans, diethylene glycol, dimethyl acetamide, dimethyl formamide, erythritol, ethanol, ethylene glycol, ethylene glycol monomethyl ether, glucose, glycerol, glycerophosphate, glyceryl monoacetate, glycine, glycoproteins, hydroxyethyl starch, inositol, lactose, magnesium chloride, magnesium, sulfate, maltose, mannitol, mannose, methanol, methoxy propanediol, methyl acetamide, methyl formamide, methyl ureas, methyl glucose, methyl glycerol, phenol, pluronic polyols, polyethylene glycol, polyvinylpyrrolidone, praline, pyridine N-oxide, raffinose, ribose, serine, sodium bromide, sodium chloride, sodium iodide, sodium nitrate, sodium nitrite, sodium sulfate, sorbitol, sucrose, trehalose, triethylene glycol, trimethylamine acetate, urea, valine and/or xylose.

In addition, in further embodiments of the invention, 1,2-propanediol may be replaced by similar concentrations of 2,3-butanediol. Similarly, dimethyl sulfoxide may be replaced by similar concentrations of glycerol or ethylene glycol or combinations thereof.

In embodiments, the cryoprotectant solution formulation may contain at least one or more of cryoprotectants that are acetamides, cyclohexanediols, formamides, polyethylene glycol, glycerol, disaccharides and propanediol.

Other cryoprotectants that may be used are described in U.S. Pat. No. 6,395,467 to Fahy et al.; U.S. Pat. No. 6,274,303 to Wowk et al.; U.S. Pat. No. 6,194,137 to Khirabadi et al.; U.S. Pat. No. 6,187,529 to Fahy et al.; U.S. Pat. No. 5,962,214 to Fahy et al.; U.S. Pat. No. 5,955,448 to Calaco et al.; U.S. Pat. No. 5,629,145 to Meryman; and/or WO 02/32225 A2, which corresponds to U.S. Pat. No. 6,740,484 to Khirabadi et al. the enclosures of which are incorporated by reference in their entireties.

The volume of the solutions employed may vary considerably, such as from about 1 to about 100 mls or greater, based upon the size of the piece of tissue being preserved, or the size of the tissue being immersed in solution.

In embodiments, the solution includes cryoprotectants in an aqueous solution, such as Euro-Collins solution, sterile water, salt solutions, culture media, and any physiological solution. Euro-Collins solution (EC-Solution) is an aqueous solution described in Table 2 below.

TABLE 2

Euro-Collins*

| Compound | mM | g/l |
|---|---|---|
| Dextrose | 194 | 34.96 |
| $KH_2PO_4$ | 15 | 2.06 |
| $K_2HPO_4$ | 42 | 7.40 |
| KCl | 15 | 1.12 |
| $NaHCO_3$ | 10 | 0.84 |

*pH = 7.4
*milliosmolality = 350-365 milliosmolal

Other examples of suitable aqueous solutions are discussed in Tables 3 and 4 below.

TABLE 3

Modified RPS-2

| Compound | mM | g/l |
|---|---|---|
| Dextrose | 180 | 32.43 |
| $K_2HPO_4$ | 7.2 | 1.25 |
| KCl | 28.2 | 2.11 |
| $NaHCO_3$ | 10 | 0.84 |
| Glutathione | 5 | 1.53 |
| Adenine HCl | 1 | 0.17 |
| $CaCl_2$ | 1 | 0.111 |
| $MgCl_2$ | 2 | 0.407 |

(Note: RPS-2 ™ solution is modified RPS-2 without $CaCl_2$ and also without $MgCl_2$)

TABLE 4

| Modified UW Solution #1 | | | Modified UW Solution #2 | | |
|---|---|---|---|---|---|
| Compound | mM | g/l | Compound | mM | g/l |
| $NaH_2PO_4 \cdot H_2O$ | 25 | 3.45 | $NaH_2PO_4 \cdot H_2O$ | 25 | 3.45 |
| K gluconate | 100 | 23.42 | K gluconate | 100 | 23.42 |
| Mg gluconate | 1 | 0.21 | Mg gluconate | 1 | 0.21 |
| glucose | 5 | 0.90 | glucose | 15 | 2.70 |
| glutathione | 3 | 0.92 | glutathione | 3 | 0.92 |
| adenosine | 5 | 1.34 | adenosine | 5 | 1.34 |
| HEPES | 10 | 2.38 | HEPES | 10 | 2.38 |
| adenine (hydrochloride) | 1 | 0.17 | adenine (hydrochloride) | 1 | 0.17 |
| ribose | 1 | 0.15 | ribose | 1 | 0.15 |
| $CaCl_2$ | 0.05 | 0.0056 | $CaCl_2$ | 0.05 | 0.0056 |
| HES(g) | — | 50 | — | — | — |

(Note: Modified UW Solution #2 does not contain HES but contains more glucose than modified UW Solution #1)

The vehicle for the cryoprotectant solution may be any type of solution that maintains matrix integrity under in vitro conditions. In embodiments, the vehicle generally comprises slowly penetrating solutes. In embodiments, the vehicle solution is a Euro-Collins solution containing 10 mM HEPES. HEPES is included as a buffer and may be included in any effective amount. In addition, other buffers, as well as no buffer, may be used. Alternative vehicles include, for example, the solutions discussed in Tables 2 and 3 above.

In embodiments, a majority or all of the cells of the tissue may be killed by manipulation of the magnitude of the step up in cryoprotectant concentration by the use of a single, stepwise, or gradient increase in cryoprotectant concentration. The cytotoxicity of the cryoprotectant solution may also kill the cells of the tissue. The cytotoxicity of the cryoprotectant solution increases as tissue (and solution) temperatures closer to 37° C. are achieved. In embodiments, exposing the tissue to the cryoprotectant at such temperatures may kill a majority or all of the cells of the tissue because of the increased level of cytotoxicity of the cryoprotectant solution. In embodiments, the temperature at which the tissue may be held and exposed to cryoprotectants and/or the solution temperature at which the single, stepwise, or gradient increase in cryoprotectant concentration occurs to carry out the killing of the cells of the tissue may be in the range of from about 0° C. to about 37° C., such as about 10° C. to about 37° C., or about 25° C. to about 37° C. The duration that the tissue may be immersed in such solution having an increased cryoprotectant concentration will be a function of the mass of the tissue. In embodiments, the cooling rates of such solutions may be adjusted to provide adequate cryoprotectant tissue peilneation (function of concentration and time) to prevent ice formation.

The final concentration of the cryoprotectant solution used for tissue preservation is at least 75% cryoprotectant by weight. In embodiments, the tissue to be preserved, such as a cryoprotectant-free tissue, or a substantially cryoprotectant-free tissue, which may or may not have been previously exposed to a cryoprotectant, may be immersed in (or exposed to) a single solution having a cryoprotectant concentration of at least 75% (by weight) in a single step. In embodiments, such a single step may increase the concentration of the cryoprotectant in the solution in which the tissue is immersed from less than 1M to greater than 12M, increasing the concentration of the cryoprotectant in the solution in which the tissue is immersed from less than 0.5M to greater than 15M. In embodiments, such a single step may kill a majority of the living cells present or all living cells present (e.g., by exposure to the extreme conditions, such as severe osmotic stresses and/or chemical cytotoxicity). In embodiments, the tissue may be immersed in solution having a cryoprotectant concentration of at least 75% (by weight) for a time sufficient for the cryoprotectant to permeate the tissue, such as at least 15 minutes, or at least 60 minutes, or at least 120 minutes.

In embodiments, the tissue to be preserved may be immersed in (or exposed to) a solution in which the cryoprotectant concentration of the solution may be gradually increased, such as by use of a linear or nonlinear concentration gradient, to achieve a final solution having a cryoprotectant concentration of at least 75% by weight cryoprotectant. In embodiments, the concentration gradient is a linear or nonlinear concentration gradient in which a cryoprotectant-free solution is gradually replaced with a solution having a cryoprotectant concentration of at least 75% by weight. In embodiments, the rate at which the cryoprotectant-free solution is replaced with a solution having a cryoprotectant concentration of at least 75% by weight may be high enough to kill a majority of the living cells present or all living cells present (e.g., by exposure to the extreme conditions, such as severe osmotic stresses and/or chemical cytotoxicity). For example, the cryoprotectant-free solution may be substantially (at least 99% by weight) replaced by a solution having a cryoprotectant concentration of at least 75% by weight in less than about 120 minutes, such as less than about 30 minutes, or less than about 10 minutes, or less than about 1 minute. In embodiments, the rate at which the cryoprotectant-free solution is replaced with a solution having a cryoprotectant concentration of at least 75% by weight may be low enough not to kill a majority of the living cells present or all living cells present, such rates will depend on the specific tissue and tissue size. In embodiments, the change in concentration in the gradient process is slow enough to achieve approximate osmotic equilibration.

In embodiments, the concentration of the solution is increased in a stepwise manner to achieve a solution having a cryoprotectant concentration of at least 75% by weight. For example, in embodiments, the concentration of the cryoprotectant may be added stepwise to achieve a particular plateau, which may be maintained for a sufficient time to achieve approximate osmotic equilibration, such as for at least 10 minutes, such as for about 15 minutes. Then, either further cryoprotectant may be added to the first cryoprotectant solution to increase the cryoprotectant concentration or a second more concentrated solution of cryoprotectant may be substituted for the first cryoprotectant solution. Then, after maintaining the concentration for sufficient time to achieve approximate osmotic equilibration, further cryoprotectant may be added, or a more concentrated may be substituted, in one or more steps to achieve the desired concentration of at least 75% by weight eryoprotectant.

In embodiments, there may be any number of cryoprotectant concentration plateaus, such as any integer between 2 and 10, before reaching the desired concentration of at least 75% by weight cryoprotectant. For example, in embodiments, four cryoprotectant concentration plateaus may be used before reaching the desired concentration of at least 75% by weight cryoprotectant. In embodiments, there may be six steps, the first step using a cryoprotectant-free solution, which is followed by four increasing cryoprotectant concentration plateaus and then a cryoprotectant concentration of at least 75% by weight cryoprotectant. For example, in embodiments, in step 1, no cryoprotectant may be used; in step 2, about 5 to about 20%, such as about 10 to about 15%, of the final cryoprotectant concentration may be used; in step 3, about 15 to about 35%, such as about 20 to about 30%, of the final cryoprotectant concentration may be used; in step 4, about 40 to about 60%, such as about 45 to about 55%, of the final cryoprotectant concentration may be used; in step 5, about 65 to about 85%, such as about 70 to about 80%, of the final cryoprotectant concentration may be used; and in step 6, the final cryoprotectant concentration, which is at least 75% by weight cryoprotectant, may be used. Each eryoprotectant concentration step may be maintained for a sufficient time to achieve approximate osmotic equilibration. In a further embodiment, the tissue may be perfused with the solution at each step.

After the tissue has been immersed in a solution containing a concentration of cryoprotectant sufficient to reach the desired concentration of at least 75% by weight cryoprotectant, the tissue, which is maintained in a solution containing a concentration of cryoprotectant of at least 75% by weight cryoprotectant, may be rapidly cooled to a temperature between −20° C. and the glass transition temperature. The rapid cooling rate may be from about −0.5 to about −100° C. per minute. The rapid cooling rate may be generally at least about −15, −20, −25 or −30° C. per minute. For example, the average cooling rate may be from about −10 to about −80° C., such as from about −30 to −60° C. per minute, or from about −35 to −50° C. per minute, or from about −40 to −45° C. per minute. The temperature to which the tissue is cooled during this rapid cooling process is between about −20° C. and the glass transition temperature of the final cryoprotectant solution of at least 75% by weight cryoprotectant, such as between about −30° C. and about −130° C., or between about −40° C. and about −110° C.

The tissue may also undergo a slow cooling process, optionally after the rapid cooling process, in which the tissue may be cooled at an average rate less than 30° C. per minute, such as at an average rate less than 10° C. per minute to a predetermined storage temperature above the glass transition temperature. The cooling process may be conducted at an average rate less than 5° C. per minute. In embodiments, the rate of cooling during this entire step does not increase above 30° C. per minute, such as a rate of cooling that does not increase above 10° C. per minute, or a rate of cooling that does not increase above 5° C. per minute. In embodiments, cooling rates (for single or multi-step cooling processes) include, for example, cooling rates in the range from about 0.5 to about 10° C./min, such as about 2 to about 8° C./min, or about 4 to about 6° C./min. In embodiments, the process is independent of cooling rate as long as ice formation is avoided.

In embodiments, a first cooling rate may be faster than the second cooling rate; however, in embodiments, the two cooling rates may be the same.

In embodiments, a slow cooling rate is achieved by changing the environment in which the container containing the solution is placed. In embodiments, a rapid cooling rate is achieved by placing the container in a liquid, such as 2-methylbutane, that has been pre-cooled to a temperature below −100° C., such as near the glass transition temperature of the solution to be cooled. Then, to achieve the slow cooling rate, the container is removed from the liquid and cooled in a gaseous environment at a temperature above the glass transition temperature. In embodiments, the glass transition temperature of the cryoprotectant solution may be about −120° C. to −135° C. under normal atmospheric conditions.

The tissue may be stored for long period of time at a temperature less than −20° C., but above the glass transition temperature. For example, the tissue may be stored at temperature between the glass transition temperature of the cryoprotectant solution and −20° C., such as about 10° C. to 80° C. above the glass transition temperature of the final (or full strength) cryoprotectant solution with at least 75% by weight cryoprotectant, or about 20° C. to 50° C. above the glass transition temperature of the final (or full strength) cryoprotectant solution with at least 75% by weight cryoprotectant. In the storage step, storing the tissue at a temperature above the glass transition temperature prevents cracking and ice formation.

In embodiment, tissues such as heart valves may be stored at about −80° C.

In embodiments, the method may further comprise transporting step, wherein the tissue is transported. In embodiments, the tissue is transported at a temperature between the glass transition temperature of the first solution and −20° C., such as about 20° C. to 80° C. above the glass transition temperature of the full strength cryoprotectant solution with at least 75% by weight cryoprotectant, or 40° C. to 60° C. above the glass transition temperature of the full strength cryoprotectant solution with at least 75% by weight cryoprotectant. For example, the tissue may be transported on dry ice at about −79.6° C.

After storage the tissue may be removed from the at least 75% by weight cryoprotectant solution with or without perfusion. Methods for removing the tissue from the at least 75% by weight cryoprotectant solution may comprise slowly warming the tissue in the at least 75% by weight cryoprotectant solution to warmer temperature in the range between −20° C. and the glass transition temperature of the cryoprotectant solution with at least 75% by weight cryoprotectant. A slow warming rate below 50° C. per minute may be used to warm the tissue in the at least 75% by weight cryoprotectant solution. In embodiments, the average warming rate during this stage may be from about 10-40° C. per minute, such as from about 25-35° C. per minute. In addition, the temperature to which the stored tissue is slowly warmed may be between about −30° C. and −80° C., such as between about −45° C. and −65° C.

After the tissue has undergone this optional slow warming process, the tissue may then be rapidly warmed to a temperature above −20° C. In embodiments, the temperature should be sufficiently high that the solution is sufficiently fluid that the tissue may be removed therefrom. The rapid warming process may be conducted at a rate above about 80° C. per minute, such as above about 100° C. per minute. The average warming rate during this step may be from about 200-300° C. per minute, such as from about 215-250° C. per minute. In embodiments, the tissue may be warmed to a temperature above about −20° C., such as above about −10° C., or to a temperature above about −5° C., such as between about −5° C. and about 5° C. In embodiments, the process is independent of warming rate as long as ice formation is avoided.

In embodiments, the rapid warming rate may be achieved by changing the environment in which the container containing the solution is placed. In embodiments, the slow warming rate may be achieved by placing the container in a gaseous environment at a temperature above the temperature at which the tissue has been stored. Then, to achieve the rapid warming rate, the container may be placed in a liquid, such as an aqueous solution of, for example, dimethyl sulfoxide (DMSO), at a temperature above −75° C., such as above 0° C., or at normal atmospheric temperatures.

In embodiments, after the tissue has been warmed to a temperature above −65° C., the concentration of the cryoprotectant in the solution may be reduced in a single, gradient, or stepwise manner. In embodiments, the tissue (such as a tissue that has been immersed in the least 75% by weight cryoprotectant solution) in which the concentration of the cryoprotectant is to be reduced may be immersed in (or exposed to) a cryoprotectant-free solution or substantially cryoprotectant-free solution in a single step. In embodiments, such a single step may decrease the concentration of the cryoprotectant in the initial solution and form a substantially cryoprotectant-free solution; for example, the concentration of the solution in which the tissue is immersed may be decreased from greater than 12M to less than 1M in a single step (or multiple steps), such as from greater than 15M to less than 0.1M in a single step (or multiple steps). In embodiments, such a step may kill a majority of the living cells present or all living cells present (e.g., by exposure to the extreme conditions, such as severe osmotic stresses and/or chemical cytotoxicity). In embodiments, the tissue may be immersed in the cryoprotectant-free solution or substantially cryoprotectant-free solution for a time sufficient for the cryoprotectant to exit the tissue, such as at least 15 minutes, or at least 60 minutes, or at least 120 minutes.

In embodiments, the tissue in which the cryoprotectant concentration is to be reduced may be immersed in (or exposed to) a solution in which the cryoprotectant concentration of the solution is may be gradually decreased, such as a by use of a linear or nonlinear concentration gradient, to achieve a substantially cryoprotectant-free solution or cryoprotectant-free solution. In embodiments, the concentration gradient is a linear or nonlinear concentration gradient in which a solution having a cryoprotectant concentration of at least 75% by weight is gradually replaced with a cryoprotectant-free solution. In embodiments, the rate at which the solution having a cryoprotectant concentration of at least 75% by weight is replaced by the cryoprotectant-free solution may be high enough to kill a majority of the living cells present or all living cells present (e.g., by exposure to the extreme conditions, such as severe osmotic stresses and/or chemical cytotoxicity). For example, the solution having a cryoprotectant concentration of at least 75% by weight may be substantially (at least 99% by weight) replaced by a cryoprotectant-free solution in less than about 30 minutes, such as less than about 10 minutes, or less than about 5 minutes, or less than about 1 minute. In embodiments, the rate at which solution having a cryoprotectant concentration of at least 75% by weight is replaced with a cryoprotectant-free solution may be low enough not to kill a majority of the living cells present or all living cells present, such rates will depend on the specific tissue and tissue size. In embodiments, the change in concentration in the gradient process is slow enough to achieve approximate osmotic equilibration.

In embodiments, the cryoprotectant concentration is reduced in a step-wise manner. In embodiments, decreasing the cryoprotectant concentration of the tissue may be achieved by immersing the tissue in a series of decreasing cryoprotectant concentration solutions to facilitate elution of cryoprotectants from the tissue. The tissue may also be perfused with the solutions. The solutions are generally at a temperature above about −15° C., such as between about −15° C. and about 15° C., or between about 0° C. and about 10° C.

In embodiments, the cryoprotectant concentration may be reduced to achieve a particular plateau, which may maintained for a sufficient time to achieve approximate osmotic equilibration, for example for at least about 10 minutes, such as for about 15 minutes. Then, the cryoprotectant concentration may be further reduced, which may or may not provide for a cryoprotectant-free solution. If not, after maintaining the concentration for sufficient time to achieve approximate osmotic equilibration, the cryoprotectant concentration may be again further reduced in one or more steps to eventually provide a cryoprotectant-free solution. In embodiments, the tissue may be immersed in each solution for at least 15 minutes, or longer than an hour.

In embodiments, a majority or all of the cells of the tissue may be killed by manipulation of the magnitude of the step down in cryoprotectant concentration by the use of a single, stepwise, or gradient decrease in cryoprotectant concentration. As discussed above, the cytotoxicity of the cryoprotectant solution may also be used to kill a majority or all of the cells of the tissue. In embodiments, temperature at which the tissue may be held and/or the temperature at which the single, stepwise, or gradient decrease in cryoprotectant concentration occurs to carry out the killing of the cells of the tissue may be in the range of from about 0° C. to about 37° C., such as about 10° C. to about 37° C., or about 25° C. to about 37° C. The duration that the tissue may be immersed in such solutions having a decreased cryoprotectant concentration will be a function of the mass of the tissue.

To decrease the cryoprotectant concentration, the cryoprotectant solution may be mixed with a solution of a type similar to the cryoprotectant-free solution utilized in adding cryoprotectant to the tissue. The solution may also comprise at least one osmotic buffering agent.

As used herein, "osmotic buffering agent" means a low or high molecular weight non-penetrating extracellular solute that counteracts the osmotic effects of the greater intracellular than extracellular concentrations of cryoprotectant during the cryoprotectant efflux process.

As used herein "non-penetrating" means that the great majority of molecules of the chemical do not penetrate into the cells of the tissue but instead remain in the extracellular fluid of the tissue.

As used herein, "low molecular weight" refers, for example, to a relative molecular mass of 1,000 daltons or less. As used herein, "low molecular weight osmotic buffering agents" have a relative molecular mass of 1,000 daltons or less. Low molecular weight osmotic buffering agents include, for example, maltose, potassium and sodium fructose 1,6- diphosphate, potassium and sodium lactobionate, potassium and sodium glycerophosphate, maltopentose, stachyose, mannitol, sucrose, glucose, maltotriose, sodium and potassium gluconate, sodium and potassium glucose 6-phosphate, and raffinose. In embodiments, the low molecular weight osmotic buffering agent is at least one of mannitol, sucrose and raffinose.

As used herein, "high molecular weight" refers, for example, to a relative molecular mass of from greater than 1,000 to 500,000 daltons. As used herein, "high molecular weight cryoprotectant and osmotic buffering agents" generally have a relative molecular mass of from greater than 1,000 to 500,000 daltons. High molecular weight osmotic buffering agents include, for example, hydroxyethyl starch (HES), polyvinylpyrrolidone (PVP), potassium raffinose undecaacetate (>1,000 daltons) and Ficoll (greater than 1,000 to 100,000 daltons). In embodiments, the high molecular weight osmotic buffering agent is HES, such as HES having a molecular weight of about 450,000.

The cryoprotectant-free solution may contain less than about 500 mM of an osmotic buffering agent, such as from about 200 to 400 mM osmotic buffering agent. As the osmotic buffering agent, a low molecular weight osmotic buffering agent may be used. In embodiments, the low molecular weight osmotic buffering agent is mannitol.

In embodiments, the cryoprotectant may be removed in a series of steps such as three, four, five, six, seven, etc. steps. In embodiments, the cryoprotectant may be removed in a series of seven steps, where in step 1, the tissue may be exposed to a cryoprotectant solution with a concentration that may be about 40 to about 80%, such as about 55 to about 75%, of the highest cryoprotectant concentration used; in a step 2, the tissue may be exposed to a cryoprotectant concentration that may be about 30 to about 45%, such as about 35 to about 40%, of the highest cryoprotectant concentration used; in step 3, the tissue may be exposed to a cryoprotectant concentration that may be about 15 to about 35%, such as about 20 to about 30%, of the highest cryoprotectant concentration used; in step 4, the tissue may be exposed to a cryoprotectant concentration that may be about 5 to about 20%, such as about 10 to about 15%, of the cryoprotectant concentration used; and in step 5, the tissue may be exposed to a cryoprotectant concentration that may be about 2.5 to about 10%, such as about 5 to about 7.5%, of the cryoprotectant concentration used. In the above steps, the remainder of the solution may be cryoprotectant-free solution containing osmotic buffering agent. In step 6, essentially all of the cryoprotectant may be removed and the osmotic buffering agent may be retained. In step 7, the osmotic buffering agent may be removed. In embodiments, steps 6 and 7 may be combined in a single step. For example, the osmotic buffering agent may be removed at the same time as the remainder of the cryoprotectant. In embodiments, if no osmotic buffering agent is used or if it is not removed, step 7 can be eliminated. Each of these concentration steps may be maintained for a sufficient time to achieve approximate osmotic equilibration, such as about 10 to 30 minutes, or 15 to 25 minutes. In embodiments, the cryoprotectant is removed in one or more washes employing a cryoprotectant-free solution.

The temperature of the series of solutions used for removing the cryoprotectant from the tissue may be above about −15° C., such as between about −15 and about 15° C., or between about 0° C. and about 37° C. In embodiments, step 1 may be started when the tissue is at a temperature above about −75° C., such as above −65° C. In embodiments, the temperature of the tissue may be below the temperature of the solution in which it is immersed in step 1, and the tissue may be further warmed to a temperature above about −15° C. during step 1 of the cryoprotectant removal.

The cryoprotectant-free solution employed for washing of the tissue may be sterile water, a physiological salt solution (for example saline, Hank's Balanced Salt Solution, Lactated Ringers Solution or Krebs-Henseliet Solution) or tissue culture media (for example Roswell Park Memorial Institute media, Dulbecco's Modified Eagle's Medium (DMEM), Eagle's Medium or Medium 199) employed for tissues, such as mammalian cells.

The number of washes, volume of each wash and duration of each wash may vary depending upon the tissue mass and the final residual chemical concentrations desired. In embodiments, the last wash (rinse) may be in a commonly employed medical salt solution, such as saline or Ringers Solution.

The tissue may be further processed after storage. For example, after storage the tissues may be seeded with patient cells. Thus, these ice-free preserved tissues may provide materials for the manufacturing of more complex tissue engineered implants for medical applications.

EXAMPLES

Example 1

Tissue Preparation

In the examples, groups of six pulmonary valves preserved with either FC or IFC were implanted in an orthotopic juvenile sheep model. See Stock. U. A., Nagashima, M., Khalil, P. N. et al., J Thorac Cardiovasc Surg 119:732-40 (2000), tissue engineered three leaflet heart valves. Sheep closely mimic human anatomy and physiology with similar annulus size, equivalent heart rate, cardiac output and little somatic growth. See Gallegos, R. P., Nockel, P I, Rivard, A. L., Bianco, R. W., J Heart Valve Disease 14:423-432 (2005), the current state of in-vivo pre-clinical animal models for heart valve evaluation.

Two different strains of sheep (crossbred Whiteface vs. Heidschnucke, a nordic short tailed breed) were chosen to guarantee a true allogeneic model.

Hearts of 15 adult, crossbred Whiteface sheep (9 ewes and 5 rams) were obtained from a slaughterhouse in Minnesota using aseptic conditions. The hearts were rinsed with lactated Ringer solution and placed in sterile Dulbelco's modified Eagle medium (DMEM, Invitrogen, Carlsbad/Calif., USA) and shipped overnight to the processing laboratory (Cell&Tissue Systems, North Charleston, S.C.). Pulmonary valves were excised aseptically. Valves were placed individually in 100 ml volumes of DMEM containing 4.5 mg/l Glucose with 126 mg/L Lincomycin, 52 mg/L Vancomycin, 157 mg/l Cefoxitin and 117 mg/l Polymixin for storage overnight at 4° C. The valves were then randomly allocated to cryopreservation by either frozen or ice-free cryopreservation.

Frozen Cryopreservation (FC) and Storage

FC was previously described in detail. See Ann Thorac Surg 81:918-26 (2006), Impact of Cryopreservation on extracellular matrix structures of heart valve leaflets. A standard protocol, according to American Association of Tissue Banks (AATB) guidelines, was applied. See Standards for Tissue Banking. 11th Edition, American Association of Tissue Banks, 2006. This protocol requires a control rate freezer, storage in nitrogen-cooled tanks and a continuous supply of liquid nitrogen.

Following antibiotic treatment, the FC valves were placed individually in sterile polyester bags containing 70-80 ml of cold cryoprotective solution (90 ml M199 containing 10 ml 10% dimethyl sulfoxide (DMSO, $Me_2SO$, Sigma, St. Louis/

Mo., USA) in DMEM). Each bag was evacuated of air, heat-sealed and controlled-rate frozen at −1° C./minute for 60 minutes from 4° C. up to −80° C. The valves were then placed and stored in the vapor phase of a liquid nitrogen storage freezer at approximately −160° C. After 1 year of storage, the valves were shipped in a nitrogen dry shipper from North Charleston, S.C. (USA) to Berlin (Germany) for implantation.

Rewarming after FC

FC valves were thawed as previously described. See Ann Thorac Surg 81:918-26 (2006). Immediately prior to implantation, FC valves were removed from the nitrogen dry shipper and placed on dry ice for 45 minutes. They were then rapidly thawed for 10 minutes in a 37° C. water bath. Bags were externally cleaned using 70% ethanol.

The cryopreservation solution was then removed in three steps by placing the valves for 15 minutes in pre-cooled DMEM with 0.5 M mannitol, followed by DMEM with 0.25 M mannitol and finally in DMEM alone. Eventually the valves were transferred to fresh DMEM and stored on ice until implantation.

Ice-Free Cryopreservation (IFC) and Storage

IFC was achieved by gradually infiltrating the heart valve tissues in six 15-minute-steps at 4° C. with increasing concentrations of a pre-cooled cryopreservation solution (CS) to achieve a final concentration of 12.6 mol/L (CS 83 wt %; made up of three components: 4.65 mol/L DMSO, 4.65 mol/L formamide and 3.31 mol/L 1,2-propanediol (all Sigma-Aldrich) in Euro-Collins solution (EC-Solution)). See Song, Y. C., Khirabad,i B. S., Lightfoot, F. G., Brockbank, K. G. M., Taylor, M. J., Nature Biotech 18: 296-299 (2000), vitreous cryopreservation maintains the function of vascular grafts.

After the final step the heart valves were placed individually in sterile polyester bags containing 70-80 ml of the cryopreservation solution. A dummy sample was established with a built-in, non-intrusive thermocouple in the center of the heart valve/bag attached to a digital thermometer to monitor experimental temperatures during cryopreservation. Each bag was evacuated of air, heat-sealed and cooled at 5.4° C./min to −100° C. in a pre-cooled bath of 2-methylbutane (isopentane). The bags were then stored at −80° C. for one year.

After 1 year of storage, the valves were shipped to the implantation site Berlin (Germany) on dry ice. Valves were stored at −80° C. until implantation.

An 83 wt % cryopreservation formulation was employed, and no ice was observed at the −80° C. storage temperature. In contrast, ice was observed when 55-70 wt % cryopreservation formulations were used.

In the above examples, a stepwise addition protocol was employed for the cryoprotectants to achieve the final formulation concentration. However, the cryoprotectant formulation maybe added in a single step, many steps or as a gradient.

The solutions in which the valves were placed remained clear, free of both cracks and ice, at all time points including post-cooling, upon placement into dry ice for transport and both before and during rewarming.

According to the above, the tissue was stored at above the glass transition temperature of the cryoprotectant formulation and below −20° C., without cracking or ice formation.

Rewarming after IFC

Each valve was placed in a 37° C. water bath until the solution moves freely. The valve was then transferred onto ice and the bag externally cleaned with 70% ethanol. The valve was rinsed briefly in ice-cold EC-Solution containing 200 mM mannitol. Then 3 sequential rinses were performed for 15 minutes each with continuous careful agitation in ice-cold EC-Solution with 200 mM mannitol, followed by EC-Solution alone and finally DMEM. The valves were stored on ice in DMEM until implantation.

The valves were then stored on ice in DMEM until implantation. All valves were rinsed in a medical grade salt solution prior to implantation.

Shipment

FC valves also required shipment in nitrogen dry shippers to the implantation site where the valves need to be kept in nitrogen-cooled freezers until implantation. In contrast, none of this expensive equipment and supply of nitrogen was needed for the IFC valves. For FC valves, the only equipment required was at −80° C. storage freezer and shipping was achieved using an insulated box with dry ice.

The IFC method facilitates preservation, storage and shipping significantly. In particular, in developing countries with limited financial and logistic resources IFC will enable allograft transplantation.

Implantation and Follow-Up

After approximately one year of storage, the valves were implanted in the orthotopic position of 12 Heidschnucke sheep.

Groups of six pulmonary valves preserved with either FC or IFC were implanted in an orthotopic juvenile sheep model. 12 juvenile sheep (average age 28 weeks±2 weeks, weight 21 kg±4 kg) underwent replacement of the pulmonary valve and main pulmonary artery with either FC or IFC allograft valves using a recently described protocol. See Stock. U. A., Nagashima, M., Khalil, P. N. et al., J Thorac Cardiovasc Surg 119:732-40 (2000).

In brief, the heart was exposed by a left anterolateral thoracotomy. Using femoral arterial and right atrial venous cannulation, normothermic cardiopulmonary bypass was established. With the heart beating a transection of the pulmonary artery (PA) was performed and a segment of the main PA and all three native leaflets were removed. The valved conduit was implanted using running 5-0 monofilament sutures (Prolene, Ethicon Inc.). No further anticoagulation was given. All animals were kept in an indoor housing facility on site and received humane care in compliance with the "Guide for the Care and Use of Laboratory Animals" published by the National Institutes of Health (NIH publication no. 85-23, revised 1985).

Follow-up of valve function was determined by two-dimensional echo-Doppler after 4, 12 and 24 weeks. After implantation, doppler echocardiography using a SonoSite Micro Max or Titan (SonoSite, Bothell, Wash., USA) equipped with a 7.5 Mhz phased-arrayed transducer was used periodically to evaluate valve function. Two-dimensional echo-Doppler examination was performed of the right ventricular outflow tract, conduit and distal main pulmonary artery after 4, 12 and 24 weeks included imaging of the conduit and leaflets from a long and short-axis view. Qualitative evaluation of pulmonary valve competence was made using color-flow Doppler mapping.

Explanation

Surviving animals were euthanized using intravenous application of embutramid. The lateral thoracotomy was reestablished and after inspection of gross morphology valves were excised and further processed.

Histology

Following euthanasia and inspection for gross morphology valves were processed for histology. Samples of each heart valve were processed as described before. See Schenke-Layland, K. et al. Ann Thorac Surg 83:1641-50 (2007). To determine general cellular and tissue morphology, representative sections were stained with Hematoxylin-Eosin (HE), Elastic Van Gieson (EVG) and Movat Pentachrome. For CD3 immunohistochemistry a cross-reactive primary antibody (DCS, Hamburg, Germany) was applied. For calcium deposition a von Kossa stain was performed.

After staining all sections were dehydrated in ethanol (Mallinckrodt Baker Inc., Deventer, Netherlands), cleared in xylene (Merck KGaA, Darmstadt, Germany), mounted using Entellan® (Merck), analyzed and documented using routine bright-field light microscopy (Axio Observer Zl, Carl Zeiss, Göttingen, Germany).

Near-Infrared (NIR) Multiphoton Imaging

Then two randomly selected, representative sets of valve samples were processed for Near-Infrared (NIR) multiphoton imaging. See Ann Thorac Surg 81:918-26 (2006) and Ann Thorac Surg 83:1641-50 (2007). An unpaired t-test was employed for statistical analyses, differences of p<0.05 were considered statistically significant.

Representative samples of frozen and vitrified leaflet specimens (each n=6) were studied using a NIR femtosecond laser scanning microscope system as described previously. See Schenke-Layland, K. et al. Ann Thorac Surg 83:1641-50 (2007). Wavelengths of 760 nm and 840 nm were employed in this study to induce ECM component dependent autofluorescence as well as second harmonic generation (SHG), See Mayer, J. E. Jr, Sem Thorac Cardiovasc Surg 7:130-132 (1995). Non-invasive serial optical horizontal sections of both, the inflow (ventricularis) and the outflow side (arterialis-fibrosa) of the different leaflet specimens were taken in z-steps of 5 μm and 10 μm. The formation of SHG radiation, which occurs at half of the incident laser wavelength, was proved with a filter FB420-10 (Thorlabs Inc., Newton/N.J., USA) in front of the detector. A 700 nm short pass filter (E700SP, Chroma Technology, Brattleboro/Vt., USA) was used to block UV radiation (transmission range: 390 nm-700 nm) and to prevent the scattered laser radiation from reaching the detector.

Viability Assessment

The alamarBlue™ assay was used to assess cell viability in heart valve tissues by measuring the oxidation/reduction reactions that take place within the cells in either leaflet, muscle or arterial conduit associated with each valve. The alamarBlue™ was added directly to the plates containing tissues in culture media and incubated for 3-6 hours at 37° C.

Upon reduction, alamarBlue™ changed color and this color change was measured using the Gemini EM fluorescent microplate reader (Molecular Dynamics) at an excitation wavelength of 544 nm and an emission wavelength of 590 nm.

Table 5 shows viability of ice-free and cryopreserved by freezing valve tissues.

TABLE 5

| Treatment | Leaflet* | Muscle | Pulmonary Artery |
|---|---|---|---|
| Ice-free valve #2 | 111 | 262 | 81 |
| Ice-free valve #5 | 61 | 245 | 87 |
| Frozen with 10% DMSO valve #10 | 4914 | 768 | 969 |

*All data expressed as relative florescent units/mg of tissue dry weight.

Viability of ice-free sheep heart valves and valves which were cryopreserved by freezing sheep heart valves was assessed. As shown in Table 5, viability was negligible within the ice-free tissues compared with the high anticipated cell viability that was preserved in cryopreserved by freezing tissues.

Two IFC and three FC animals were lost in the process of follow-up due to either surgical complications or bacterial endocarditis. In the surviving FC-group, severe valvular stenosis with subsequent right heart failure was observed. This observation correlated with echo data at 6 months revealing significantly increased pressure gradients in the FC-group compared to IFC-group (mean 35 versus 14 mmHg, p<0.05).

Haemodynamic Results

In the FC-group severe valvular stenosis with subsequent right heart failure was observed. This observation correlated with echo data at 6 months, revealing increased pressure gradients in the FC-group compared to IFC-animals with a mean of 35 versus 14 mmHg.

Gross Morphology Results

Figure 1:
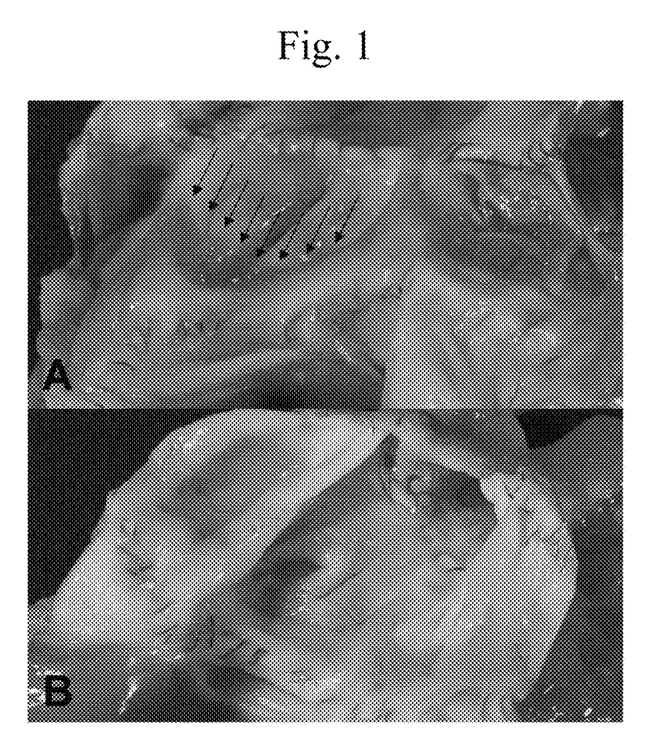
FIG. 1 demonstrates the gross morphology of explanted pulmonary heart valves after 7 months implantation in the orthotopic position.

FIG. 1 demonstrates the gross morphology of explanted pulmonary heart valves after 7 months implantation in the orthotopic position. FIG. 1A shows frozen cryopreserved (FC) heart valve with thickening of the leaflets (arrows). FIG. 1B shows vitreous cryopreserved (IFC) heart valve with normal appearance of the leaflets.

As shown in FIG. 1A, in the FC-group, gross morphology showed that frozen cryopreserved (FC) heart valve significantly thickened leaflets (arrows). In contrast, in the IFC-group, vitreous cryopreserved heart valve showed normal appearance of the leaflets.

Histology Results

Figure 2:
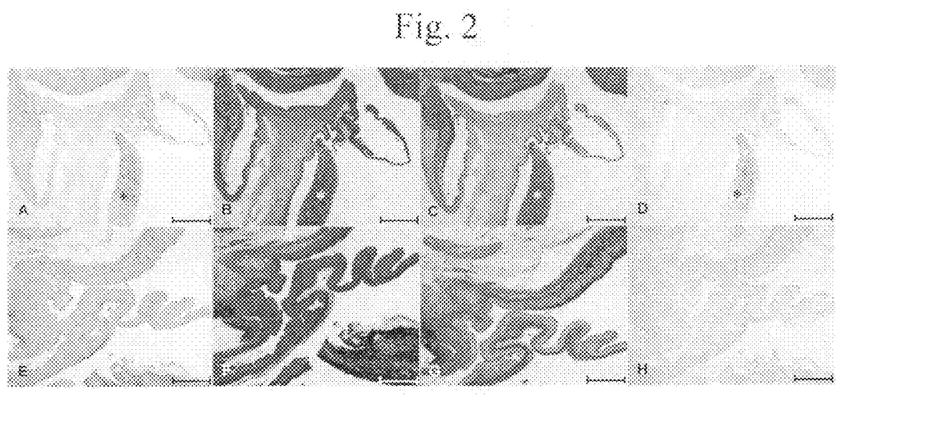
FIG. 2 demonstrates the histology of explanted pulmonary valves 7 months after implantation. FC valves are depicted in FIGS. 2A-2D, and IPC valves are depicted in FIGS. 2E-2H.

FIG. 2 demonstrates a histology of explanted pulmonary valves which are 7 months after implantation. FC valves are depicted in FIGS. 2A-2D and IFC valves are depicted in FIGS. 2E-2H.

As shown in FIGS. 2E-2H, no leaflet thickening or inflammatory cell infiltrates were observed in IFC valves. Neither group demonstrated calcification. Staining revealed a significant thickening of the FC valves (FIG. 2A) with proliferating cells and thrombus formation on the inflow side (asterisk).

In contrast, IFC showed an almost acellular ECM (FIG. 2E). EVG and Movat Pentachrome staining for ECM confirmed this observation showing extremely well maintained ECM structures in the IFC valves (FIGS. 2F and 2G). Fibrous tissue formation was observed in the FC group (FIGS. 2B and 2C). Von Kassa staining did not show significant calcification in either group (FIGS. 2D and 2H). Scale bars equal 100 μm. Conventional histology confirmed the observation in FIG. 1, and revealed the presence of chronic inflammatory cell infiltrates.

Figure 3:
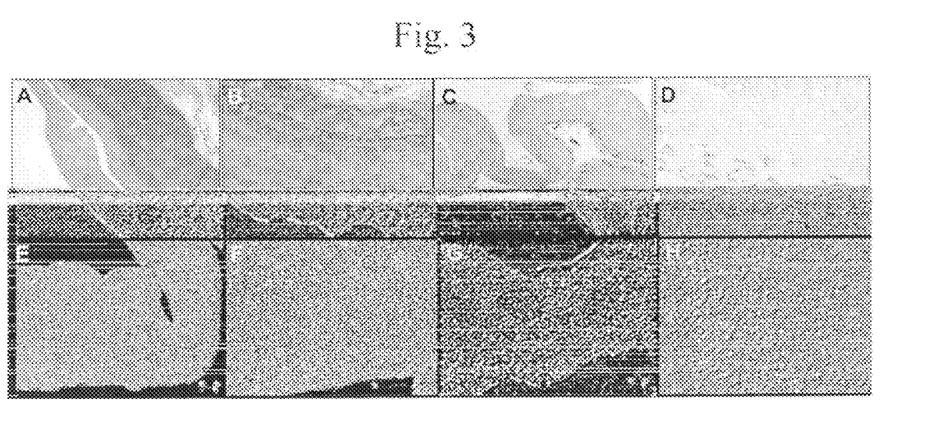
FIG. 3 demonstrates the histology of immunohistochemistry using CD3 with a cross-reactive primary antibody. IFC valves are depicted in FIGS. 3A-3D, and FC valves are depicted in FIGS. 3E-3H.

FIG. 3 demonstrates a histology of heart valve leaflets 7 months after implantation. immunohistochemistry using CD3 with a cross-reactive primary antibody (DCS, Hamburg, Germany) revealed that FC preserved heart valves demonstrate significant increased T-cell mediated inflammation in the valve stroma. In IFC heart valves, CD3 positive cells were observed exclusively in the pannus migrating along the leaflet on the ventricular side (FIGS. 3C and 3D). Conventional histology confirmed the observation in FIG. 1, and revealed the presence of chronic inflammatory cell infiltrates. In contrast, no leaflet thickening or inflammatory cell infiltrates were observed in IFC valves. Neither group demonstrated calcification.

A: (100×) Movat-pentachrome stain with clear demonstration of preserved ECM matrix (yellow=collagen, blue=proteoglycans, black=elastin)

B: (400×) same valve with higher magnification and visualization of elastic fiber structures in the ventricularis).

C: H&E stain (100×) of an almost cell free leaflet with migrating pannus formation on the ventricularis side.

D: CD3-stain of pannus formation indicating only sparse CD3 positive cells.

E: Movat-pentachrome stain (100×) of FC-leaflet with severe matrix disruption and marked thickening.

F: Higher magnification (400×) confirming matrix alteration.

G: H&E stain (100×) revealing tissue with diffuse cellular infiltration.

H: CD3-stain confirming T-cell infiltration of the entire valve stroma. Scale bars equal 100 µm.

Near-Infrated (NIR) Multiphoton Imaging Results

Figure 4:
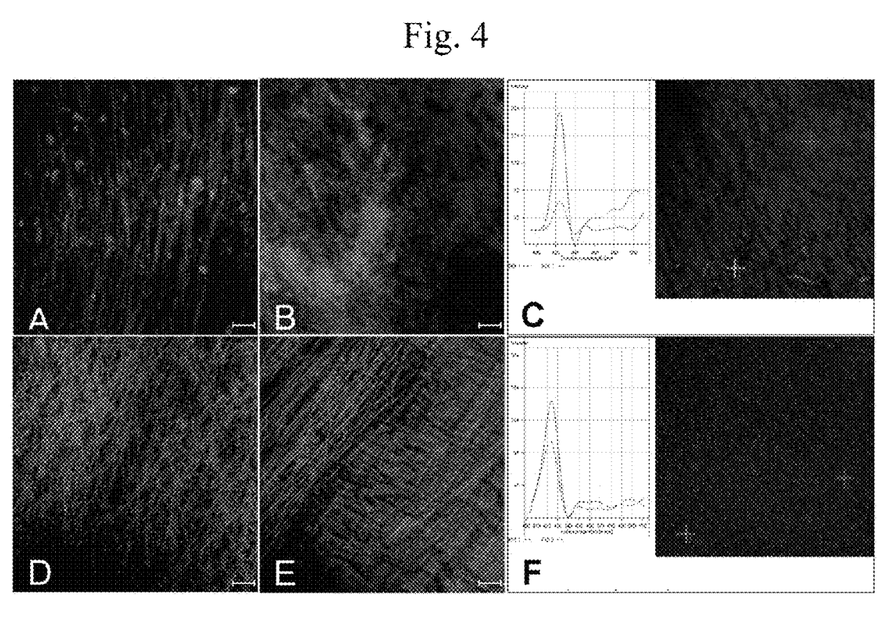
FIG. 4 demonstrates the multiphoton-excited autofluorescence imaging (FIGS. 4A, 4B, 4D and 4E) and second harmonic generation (SHG) signal profiling (FIGS. 4C and 4F) of leaflet structures.

FIG. 4 demonstrates the multiphoton-excited autofluorescence imaging (FIGS. 4A, 4B, 4D and 4E) and second harmonic generation (SHG) signal profiling (FIGS. 4C and 3F) of leaflet structures after 7 months in vivo employing laser wavelengths of 760 nm (green: elastic fibers, cells) and 840 nm (red: collagen). FIGS. 4A and 4D represent scans of elastin-rich ventricularis regions; FIGS. 4B and 4E are transition areas between ventricularis and spongiosa.

Autofluorescence images of FC tissues (FIGS. 4A and 4B) reveal deteriorated ECM leaflet structures. In contrast, the ECM structures in IFC valves (FIGS. 4D and 4E) are well preserved.

The graphs represent peak SHG and autofluorescence intensities of collagen-containing structures (red) and elastic fibers (green) in the corresponding lambda stack overlay images of FC (FIG. 4C) and IFC (FIG. 4F) leaflet outflow sides, denoted by the red and green crosses, respectively. Scale bars equal 20 µm.

As shown in FIG. 4, multiphoton imaging and second harmonic generation (SHG) microscopy revealed reduced inducible autofluorescence within ECM structures in the FC samples when exposed to 760 and 840 nm laser pulses (FIGS. 4A and 4B), and weak SHG signals from collagenous structures (FIG. 4C). In contrast, in the IFC explants we found well preserved ECM structures (FIGS. 4D and 4E), comparable to fresh tissues. Quantitative assessment of peak SHG and autofluorescence signals using spectral fingerprinting confirmed these observations (FIGS. 4C and 4F). The peak leaflet collagen SHG signal at 420 nm was significantly greater in vitrified explants than in cryopreserved explants (172+/−32 versus 137+/−11, p<0.05). This data has striking similarities to previously published in vitro analyses and indicates that there is little if any ECM repair in vivo. See Ann Thorac Surg 81:918-26 (2006) and Ann Thorac Surg 83:1641-50 (2007).

Our results demonstrate that IFC valves with preserved ECM components survived extended in vivo testing, more than 24 million wear cycles, without thickening of the leaflets or ultrastructural deterioration.

A variety of reasons for allograft heart valve failure were discussed in the past and most investigators have emphasized immunological issues. See Rajani, B., Mee, R. B., Ratliff, N. B., J Thorac Cardiovasc Surg 115:111-7 (1998), evidence for rejection of homograft cardiac valves in infants. See also Koolbergen, D. R., Hazekamp, M. G., de Heer, E. et al., J Thorac Cardiovasc Surg 124:689-97 (2002), the pathology of fresh and cryopreserved homograft heart valves: An analysis of forty explanted homograft valves.

Standard quantitative and qualitative cellular and matrix evaluations such as biochemical, immunohistochemical screening and routine histology did not help to solve the controversial discussion whether remaining allogeneic cells or potentially altered extracellular matrix contributed to the observed degeneration.

Preliminary data on patients treated with decellularized allografts has recently demonstrated that decellularization did not significantly improve outcome in terms of pressure gradients and structural deterioration compared to non-decellularized allografts. See Bechtel, J. F., Stierle. U., Sievers, H., J Heart Valve Dis 17:98-104 (2008), fifty-two months mean follow up of decellularized SynerGraft-treated pulmonary valve allografts.

These early clinical results, with a mean follow-up of 52 months, question the validity of theories that the remaining cells in allogeneic heart valves subsequently contribute to inflammation and immunoreactivity as the sole cause of structural deterioration. The formation of extracellular ice is well known to be hazardous to structured tissues and organs. See Brockbank, K. G., Lightfoot, F. G., Song, Y. C., Taylor, M. J., J Heart Valve Dis 9(2): 200-206 (2000), interstitial ice formation in cryopreserved homografts: a possible cause of tissue deterioration and calcification in vivo.

Ice crystal formation during cryopreservation was avoided by applying high concentrations of cryoprotectants to promote amorphous solidification rather than crystallization. See U.S. Pat. No. 6,740,484. Storage at −80° C. rather than below −135° C. in vapor phase nitrogen maintained the valves in a non-vitrified state above the glass transition temperature of the cryoprotectant formulation (−124° C.), and thus avoided the risk of tissue cracking that may occur in vitrified tissues during storage and transport.

Although it has been previously shown that FC accelerates degeneration in a syngeneic rodent model, the direct impact of ice formation on elastic and collagenous fiber containing tissues could not be displayed conclusively using conventional visualization methods. See Legare, J. F., Lee, D. G., Ross, D. B., Circulation 102: III75-78 (2000), cryopreservation of rat aortic valves results in increased structural failure.

The development and application of near-infrared multiphoton microscopy in combination with femtosecond laser tomographs has allowed visualization of ECM alterations with submicron resolution. See Ann Thorac Surg 81:918-26 (2006) and Ann Thorac Surg 83:1641-50 (2007).

These novel imaging technologies revealed that destruction of amorphous and particularly fibrillar matrix structures predisposes FC allografts to structural failure, while IFC allografts demonstrated matrix preservation and loss of allogeneic cell viability.

It is believed that both matrix preservation and loss of native cells in the tissue contributed to improved in vivo function. The ice-free preservation results in tissues that are less prone to inflammation than either decellularized tissues or FC preserved tissues employing current commercial practices.

In recent years the clinical acceptance of allografts has decreased significantly due to their limited long-term durability. It is anticipated that the outcome of clinical heart valve allografts will be improved by IFC, and that processing, storage and shipping will be both simpler and consequently cheaper than current FC practice. This new preservation technology is expected to display utility for preservation of various tissue matrices for other medical applications.

In the example, using allogeneic ovine pulmonary heart valves, it was shown that the ECM damage caused by FC is not restored after 7 months in vivo (equivalent to 5 years in humans). The data also demonstrate that IFC maintains crucial ECM-components such as elastin and collagen, translating into superior hemodynamic in vivo results. The IFC, explants were free of inflammatory cell infiltrates and structural degeneration. IFC also significantly reduced infrastructural needs for preservation, storage and shipping compared to currently applied FC practice.

These results have important implications for clinical valve transplantation with the promise of better long-term function, reduced re-intervention rates and lower costs. This is particularly important in developing countries with limited financial resources.

This method is applicable to other medical applications of intact extracellular tissue matrices that do not require living, viable cells. Specifically, this method is also applicable to other medical applications of intact extracellular tissue matrices of both allogeneic human and xenogeneic mammalian origin that do not require living, viable cells such as for example skin, ligament, tendon, bone, peripheral nerves, dura mater, pericardium, artery, vein, bladder, gastrointestinal tract tissues, and others. The medical applications for which these matrices may be used include but should not be limited to wound dressings, repair of bone defects, repair of blood vessels, repair of damaged peripheral and central nervous system tissues, repair of uretogenital defects and patch grafts.

Example 2

Porcine aortic artery segments were procured from a slaughter house. All tissues, both fresh controls and cryopreserved groups were treated with antibiotics at 4° C. Conventional frozen cryopreservation was realized using a 1° C./min cooling rate and a culture medium based cryoprotectant formulation containing 1.4M dimethylsulfoxide and vapor-phase nitrogen storage according to standard protocols. Ice-free cryopreservation was realized by infiltrating the tissue with 12.6 M cryoprotectant solution containing dimethylsulfoxide, formamide and 1,2-propanediol in a single step. Bags containing the vessels were cooled for 10 min in a −120° C. methylbutane bath and stored at −80° C. After rewarming and washing to remove the cryoprotectants the following assays were performed:

1) Viability testing via measurement of resazurin (alamarBlue™) reduction;
2) Histology was assessed by H&E-staining and Movat-Pentachrome;
3) Collagen and elastin were visualized via two-photon laser scanning microscopy (LSM); and
4) Hemocompatibility testing was performed using a battery of assays.

No tissue cracking was observed. Ice-free cryopreserved vessels demonstrated anticipated low viability compared with conventional frozen vessels due to the rate of addition and removal of the extremely high concentrations of potentially cytotoxic cryoprotective agents.

Routine histology and LSM revealed no structural alterations between both cryopreserved tissue groups and fresh tissue. Hemocompatibility assays (quantifying thrombin/antithrombin-III-complex, beta-thromboglobulin, inflammation marker PMN-elastase and terminal complement complex SC5b-9) revealed no significant differences between fresh, ice-free and conventional cryopreserved vessels.

These results indicate that ice-free cryopreservation is not only a potentially cost-effective preservation, storage and shipping alternative for blood vessels. It should also be a safe method because no structural or hemocompatibility marker deterioration was observed. The loss of viability associated with ice-free cryopreservation was designed in the development of the ice-free processing technique in order to reduce the immunogenicity of the tissues. It is well established that viability is rapidly lost post-implantation in conventional FC allografts due to a graft recipient immune response. After implantation, the low viability of IFC grafts is anticipated to improve clinical outcome. In conclusion, no barriers to progression to planned large animal artery implant studies were observed.

All literature and patent references cited throughout the disclosure are incorporated by reference in their entireties.

What is claimed is:
1. A method for preserving a tissue, comprising:
 (i) immersing a tissue in a solution having a cryoprotectant concentration of at least about 75%, by weight relative to the weight of the solution;
 (ii) cooling the tissue in the solution having said cryoprotectant concentration of at least about 75%, by weight relative to the weight of the solution, to a temperature between about −20° C. and the glass transition temperature of the solution having said cryoprotectant concentration of at least about 75%, by weight relative to the weight of the solution, wherein the tissue is cooled and maintained a temperature above the glass transition temperature of the solution without ice formation; and
 (iii) after the tissue reaches the temperature between about −20° C. and the glass transition temperature of the solution having said cryoprotectant concentration of at least about 75% by weight, changing the concentration of the cryoprotectant in the solution in which the tissue was cooled in step (ii) to form a substantially cryoprotectant-free solution in a single step.

2. The method of claim 1, wherein the tissue in step (i) is a cryoprotectant-free tissue or a substantially cryoprotectant-free tissue.

3. The method of claim 1, wherein step (i) further comprises: killing a majority of the living cells of the tissue, or killing all of the living cells of the tissue.

4. The method of claim 3, wherein a majority of the living cells of the tissue are killed as a result of an increase in cryoprotectant concentration in step (i), or all of the living cells of the tissue are killed as a result of an increase in cryoprotectant concentration in step (i).

5. The method of claim 4, wherein the cryoprotectant concentration is increased from a cryoprotectant concentration of less than about 1 M to a cryoprotectant concentration of greater than about 12 M.

6. The method of claim 1, wherein step (iii) further comprises: killing a majority of the living cells of the tissue, or killing all of the living cells of the tissue.

7. The method of claim 6, wherein a majority of the living cells of the tissue are killed as a result of a decrease in cryoprotectant concentration in step (iii), or all of the living cells of the tissue are killed as a result of a decrease in cryoprotectant concentration in step (iii).

8. The method of claim 7, wherein the cryoprotectant concentration is decreased from a cryoprotectant concentration of greater than about 12 M to a cryoprotectant concentration of less than about 1 M.

9. The method of claim 1, wherein in step (ii) further comprises: storing the tissue at a temperature between about −20° C. and the glass transition temperature of the solution having said cryoprotectant concentration of at least about 75%, by weight relative to the weight of the solution.

10. The method of claim 9, further comprising: (iv) obtaining a substantially cryoprotectant-free tissue or cryoprotectant-free tissue, and (v) seeding the substantially cryoprotectant-free tissue or cryoprotectant-free tissue with patient cells.

11. The method of claim 1, wherein step (1) comprises:
 (i) immersing the tissue in a series of solutions having increasing concentrations of cryoprotectant to achieve immersion in a final solution with a cryoprotectant concentration of at least about 75%, by weight relative to the weight of the solution.

12. The method of claim 1, wherein in step (i) further comprises: applying a linear or nonlinear concentration gradient in which a cryoprotectant-free solution is gradually replaced with a solution having a cryoprotectant concentration of at least about 75%, by weight relative to the weight of the solution.

13. The method of claim 12, wherein the solution having a cryoprotectant concentration of at least about 75%, by weight relative to the weight of the solution, is substantially replaced by a cryoprotectant-free solution in less than about 5 minutes.

14. The method of claim 1, wherein the solution having said cryoprotectant concentration of at least about 75%, by weight relative to the weight of the solution, in step (ii) has a glass transition temperature between about −110° C. and about −130° C.

15. The method of claim 1, wherein the tissue is cooled to a temperature between about −20° C. and about −110° C. in step (ii).

16. The method of claim 1, wherein the tissue is cooled to a temperature between about −40° C. and about −100° C. in step (ii).

17. The method of claim 1, wherein the tissue is cooled to a temperature between about −75° C. and about −85° C. in step (ii).

18. The method of claim 1, wherein the cryoprotectant concentration of at least about 75%, by weight relative to the weight of the solution, in step (i) is between about 83%, by weight relative to the weight of the solution, and about 99%, by weight relative to the weight of the solution, cryoprotectant.

19. The method of claim 1, wherein the cryoprotectant concentration of at least about 75, by weight relative to the weight of the solution, in step (i) is between about 85%, by weight relative to the weight of the solution, and about 95%, by weight relative to the weight of the solution, cryoprotectant.

20. The method of claim 1, wherein the cryoprotectant in step (i) comprises at least one molecule selected from the group consisting of acetamides, cyclohexanediols, formamides, dimethyl sulfoxide, ethylene glycol, polyethylene glycol, glycerol, disaccharides and propanediol.

21. The method of claim 1, wherein said cryoprotectant solution in step (i) comprises at least one member selected from the group consisting of acetamide, agarose, alginate, alanine, albumin, ammonium acetate, anti-freeze proteins, butanediol, chondroitin sulfate, chloroform, choline, cyclohexanediols, dextrans, diethylene glycol, dimethyl acetamide, dimethyl formamide, dimethyl sulfoxide, erythritol, ethanol, ethylene glycol, ethylene glycol monomethyl ether, formamide, glucose, glycerol, glycerophosphate, glyceryl monoacetate, glycine, glycoproteins, hydroxyethyl starch, inositol, lactose, magnesium chloride, magnesium, sulfate, maltose, mannitol, mannose, methanol, methoxy propanediol, methyl acetamide, methyl formamide, methyl ureas, methyl glucose, methyl glycerol, phenol, pluronic polyols, polyethylene glycol, polyvinylpyrrolidone, proline, 1,2-propanediol, pyridine N-oxide, raffinose, ribose, serine, sodium bromide, sodium chloride, sodium iodide, sodium nitrate, sodium nitrite, sodium sulfate, sorbitol, sucrose, trehalose, triethylene glycol, trimethylamine acetate, urea, valine and xylose.

22. The method of claim 1, wherein said tissue is a pulmonary valve or an artery.

23. A method for preserving a tissue, comprising:
  (i) immersing a cryoprotectant-free tissue or substantially cryoprotectant-free tissue in a solution having a cryoprotectant concentration of at least about 75%, by weight relative to the weight of the solution;
  (ii) cooling the tissue in the solution having said cryoprotectant concentration of at least 75%, by weight relative to the weight of the solution, to a temperature between about −20° C. and the glass transition temperature of the solution having said cryoprotectant concentration of at least about 75%, by weight relative to the weight of the solution, wherein the tissue is cooled and maintained a temperature above the glass transition temperature of the solution without ice formation; and
  (iii) immersing the tissue in a cryoprotectant-free solution.

24. The method of claim 23, wherein step (iii) comprises: in a single step, after the tissue reaches the temperature between about −20° C. and the glass transition temperature of the solution having said cryoprotectant concentration of at least about 75%, by weight relative to the weight of the solution, removing the tissue from the solution having said cryoprotectant concentration of at least about 75%, by weight relative to the weight of the solution, and immersing the tissue in a cryoprotectant-free solution.

25. The method of claim 23, wherein step (iii) comprises: immersing the tissue in a series of solutions having decreasing concentrations of cryoprotectant to obtain a cryoprotectant-free tissue immersed in a cryoprotectant-free solution.

26. A method for preserving a tissue, comprising:
  (i) immersing the tissue in a series of solutions having increasing concentrations of cryoprotectant to achieve immersion in a final solution with a cryoprotectant concentration of at least about 75%, by weight relative to the weight of the final solution;
  (ii) cooling the tissue in the final solution having said cryoprotectant concentration of at least about 75%, by weight relative to the weight of the final solution, to a temperature between about −20° C. and the glass transition temperature of the final solution having said cryoprotectant concentration of at least about 75%, by weight relative to the weight of the final solution, wherein the tissue is tooled and maintained at a temperature above the glass transition. temperature of the final solution, without ice formation; and
  (iii) immersing the tissue in a series of solutions having decreasing concentrations of cryoprotectant to obtain a substantially cryoprotectant-free tissue immersed in a substantially cryoprotectant-free solution.

\* \* \* \* \*